(12) United States Patent
Petereit et al.

(10) Patent No.: US 6,656,507 B2
(45) Date of Patent: *Dec. 2, 2003

(54) AQUEOUS DISPERSION SUITABLE FOR THE PRODUCTION OF COATINGS AND BINDERS FOR SOLID ORAL DRUGS

(75) Inventors: Hans-Ulrich Petereit, Darmstadt (DE); Silke Goelz, Bensheim (DE); Wolfgang Weisbrod, Weiterstadt (DE)

(73) Assignee: Roehm GmbH & Co. KG, Darmstadt (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/263,878

(22) Filed: Mar. 8, 1999

(65) Prior Publication Data

US 2001/0055619 A1 Dec. 27, 2001

(30) Foreign Application Priority Data

Mar. 6, 1998 (DE) .......................... 198 09 719

(51) Int. Cl.$^7$ .............................. A61K 9/16; A61K 9/14
(52) U.S. Cl. ....................... 424/490; 424/400; 424/484; 424/489
(58) Field of Search ................ 424/490, 400, 424/489, 448

(56) References Cited

U.S. PATENT DOCUMENTS 5,326,570 A * 7/1994 Rudnic et al. ............... 424/458
5,366,755 A   11/1994 Timonen et al.
5,695,784 A * 12/1997 Poellinger et al. .......... 424/495

FOREIGN PATENT DOCUMENTS

| EP | 0 468 247 A1 | 1/1992 |
|----|--------------|--------|
| EP | 0 519 870 A1 | 12/1992 |
| EP | 0 793 959 A1 | 3/1997 |
| WO | WO 96/35413 | 11/1996 |
| WO | WO 97/41839 | 11/1997 |

OTHER PUBLICATIONS

Rudnic "Oral Solid Dosage Forms" Remington: the Science and Practice of Pharmacy ed Gennaro p. 1615 1995.*
Shukla Polymethacrylates Handbook of Pharmaceutical Excipients ed Wade and Weller pp. 362–366 1994.*
Shukla, A. Polymethacrylates Handbook of pharmaceutical excipients 362–366, 1994.*
Derwent Patent Abstract EP 793959.
Derwent Patent Abstract DE 4021678.
H. Al–Hmoud et al, "A Controlled Release Matrix Using a Mixture of Hydrophilic and Hydrophobic Polymers", International Journal of Pharmaceutics, 68 (1991) R1–R3.

* cited by examiner

Primary Examiner—Thurman K. Page
Assistant Examiner—Robert M. Joynes
(74) Attorney, Agent, or Firm—Oblon, Spivak, McClelland, Maier & Neustadt, P.C.

(57) ABSTRACT

An aqueous dispersion for the production of binders or coatings for solid oral drugs having a water content of 90–40 wt. % and a solids portion of 10–60 wt. %, whereby said solids portion is composed of:

(A) 10–99 wt. % of a polymer mixture consisting of:
  (a) 75–99 wt. % of a polymethacrylate copolymer consisting of up to 98–85 wt. % of alkyl (meth) acrylate monomers with $C_1$–$C_4$ alkyl residues and up to 2–15 wt. % of alkyl (meth)acrylate monomers with a quaternary ammonium group in the alkyl residue, and (b) 25–1 wt. % of an alkali salt of carboxymethylcellulose having a weight average molecular weight of less than 150,000, and (B) 90–1 wt. % of at least one substance normally added to pharmaceutical formulations.

17 Claims, No Drawings

AQUEOUS DISPERSION SUITABLE FOR THE PRODUCTION OF COATINGS AND BINDERS FOR SOLID ORAL DRUGS

BACKGROUND OF THE INVENTION

1. Field of the Invention

The present invention relates to an aqueous dispersion suitable for the production of binders and coatings for solid oral drugs, containing as the solid portion, a polymer mixture A) consisting of a polymethacrylate copolymer and an alkali salt of carboxymethylcellulose and B) the customary added ingredients. The invention also relates to the applications of the dispersion.

2. Description of the Background

Water-soluble nonionic polysaccharide derivatives, for example, hydroxypropylmethylcellulose (HPMC), are routinely used for the granulation of tablet mixtures and for simple coating of solid drugs. Less often, soluble ionic polysaccharides, for example, sodium carboxymethylcellulose (Na—CMC), are used. However, both polymers form coatings that quickly dissolve in water and have a high permeability. Therefore, the protective and insulating effect in drugs is limited. The binding ability of these materials for pigments is also limited, so that the covering power of coatings for strongly colored cores is not sufficient. Furthermore, hydrophilic, strongly swelling polymers tend to form clumps when stirred in water, which must be avoided by means of special dissolution methods.

DE 4,021,678 A1 describes a method for the production of small formed pieces containing etofibrate, and controlled release of active ingredients by mixture of the active ingredients with a physiologically neutral colloid that is insoluble in water and one that is soluble or swells in water, and subsequent extrusion. The colloids that are insoluble in water and are water-soluble or capable of swelling can be used in a ratio of 1:10 to 90:1. Etofibrate can, for example, be mixed together with a polymethacrylic acid ester with quaternary ammonium groups (EUDRAGIT® RS) and sodium carboxymethylcellulose in the ratio 2:1. The goal is to achieve a release which is as constant as possible over a period of 4–6 h.

EP 0 793 959 describes formulations with controlled release of active ingredients that are coated with a substance that is insoluble in water and a polymer capable of swelling, that has no basic groups. In the long list of substances that can potentially be used, polymethacrylate copolymers with quaternary ammonium groups (EUDRAGIT® RS) are named among the substances that are insoluble in water. Sodium carboxymethylcellulose is listed among the substances that are capable of swelling. No concrete indication of combining these two polymers is present in the disclosure of the publication.

SUMMARY OF THE INVENTION

Accordingly, one object of the invention is to provide a coating and binder for solid oral drugs that, on one hand releases active ingredients for drugs quickly and without affecting the pH value, and on the other hand, which makes possible a good insulating effect in thin coatings, as well as high pigment binding ability and reliable protection of flavor.

Another object of the invention is to provide an aqueous polymer dispersion for drug formulations which, as an applied coating, is not impeded by swelling and adhesion.

Briefly, these objects and other objects of the invention as hereinafter will become more readily apparent can be attained by an aqueous dispersion for the production of binders or coatings for solid oral drugs having a water content of 90–40 wt. % and a solids portion of 10–60 wt. %, whereby said solids portion is composed of:

(A) 10–99 wt. % of a polymer mixture consisting of:
  (a) 75–99 wt. % of a polymethacrylate copolymer consisting of 98–85 wt. % of alkyl (meth)acrylate monomers with $C_1$–$C_4$ alkyl residues and 2–15 wt. % of alkyl (meth)acrylate monomers with a quaternary ammonium group in the alkyl residue, and (b) 25–1 wt. % of an alkali salt of carboxymethylcellulose having a weight average molecular weight of less than 150,000, and
(B) 90–1 wt. % of at least one substance normally added to pharmaceutical formulations.

DETAILED DESCRIPTION OF THE PREFERRED EMBODIMENTS

The polymer mixture A consisting of components (a) and (b) in the stated quantity ratio is decisive for the properties of the coatings and binders for solid oral drugs which are produced from the dispersion. In the process, it is indispensable for the two components to be present in an aqueous medium, because the advantageous effects cannot be achieved when an organic solution is used (see Comparison Example 19). It is presumed that polymers (a) and (b) aggregate with one another in an advantageous manner in the aqueous phase either first in the dispersion itself or during the application of the dispersion, or during the evaporation of the water. Surprisingly, by increasing the quantity of component (b), there is an increase in tensile strength of the coated product, but a reduction of elongation at break. The binders or coatings that can be produced from the dispersion have a good mechanical strength (see Example 10), but disintegrate, as desired, very quickly in artificial gastric juice. The release of the active ingredients is practically constant and independent of the pH. In fact, disintegration of the prepared pharmaceutical coatings occurs in less than 30 min for a polymer coating of 2 mg/cm$^2$ in artificial gastric juice. The protection of flavor is very reliable (see Example 9), and the pigment binding ability is high (see Example 8).

Water Content and Particle Size

The water content of the dispersion is in the customary range of 90–40 wt. %, preferably 80–50 wt. %. The average particle size of the particulate matter in the dispersion is in the range of 50–500 nm.

Polymer Mixtures A

Component (a)

A portion of polymer mixture A consisting of components (a) and (b), to a large extent insoluble in water, is formed by a (meth)acrylate copolymer (a) that consist of up to 98–85 wt. %, preferably up to 96–88 wt. %, of alkyl (meth)acrylate monomers with $C_1$–$C_4$ alkyl residues, and up to 2–15 wt. %, preferably up to 4–12 wt. % of alkyl (meth)acrylate monomers having a quaternary ammonium group in the alkyl residue.

Suitable alkyl (meth)acrylate monomers having $C_1$–$C_4$ alkyl residues include methyl acrylate, ethyl acrylate, butyl acrylate, butyl methacrylate, and methyl methacrylate. The copolymer contains 20–40 wt. %, especially 25–35 wt % ethyl acrylate and 50–70 wt. %, especially 55–70 wt. % methyl methacrylate.

Suitable alkyl (meth)acrylate monomers having quaternary ammonium groups can be found, for example, in EP 0

181 515. Disclosed Examples include acryl and methacryloxytrimethylammonium chloride or the methosulfate, benzyldimethylammonium methyl methacrylate chloride, diethylmethylammonium ethyl acrylate and methacrylate methosulfate, N-trimethylammonium propyl methacrylamide chloride and N-trimethylammonium 2,2-dimethylpropyl-1-methacrylate chloride. 2-Trimethyl ammonium methyl methacrylate chloride is specially preferred.

Preferably, the (meth)acrylate copolymer having quaternary ammonium groups corresponding to component (a), can be composed of 65 or 60 wt. % methyl methacrylate, 30 wt. % ethyl acrylate and 5 or 10 wt. % 2-trimethylammonium methyl methacrylate chloride (EUDRAGIT® RS or RL).

The copolymers (a) are obtained by known techniques such as radical, solution, bead, or emulsion polymerization. They can be present as an extruded granulate, ground or spray-dried powder, or as a dispersion, for example, with 30 wt. % solid material.

Component (b)

The water-soluble component (b) of polymer mixture A consisting of components (a) and (b) is formed by alkali salts of carboxymethylcellulose having a molecular weight (weight average) of less than 150,000, preferably 5,000–100,000, especially preferably, 7,000–70,000. If the molecular weight of component (b) is 150,000 or more, there may be a thickening of the batch may occur, so that it can practically no longer be processed. Suitable alkali salts include lithium, sodium and potassium, as well as ammonium salts. Preferably, sodium salts are used. The viscosity of a 2% solution in water at 20° C. is usually in the range of 1–200 mPas, preferably 2–60 mPas. Preferably such types are used which, because of their method of production, contain only small portions of native fiber.

Mixture Ratio of Components (a) and (b)

The amount of component (b) employed is 1–25 wt. %, preferably 5–15%, especially preferably 5–10 wt. %, relative to the amount of polymethacrylate that is insoluble in water.

The dispersions of the invention can be produced by mixing components (a) and (b) in powder form (see Example 13), or in the molten state (see Example 14), and in each case, subsequent absorption in water. The two components may also be present already as a dispersion or aqueous solution, and can be mixed directly (see Example 15). An extrusion of the powder mixture with subsequent comminution to ensure an even distribution of the two components and then absorption in water is also a practical technique.

Processing into a film is done by drying, preferably during application of the spray. The energy required for evaporation of the water can be obtained by the heated process air generated, by microwaves, or by other radiation, optionally in a vacuum as well.

Fundamentally, the polymers used must be nontoxic and they must present no risk to patients when used in pharmaceutical agents.

B) Customary Additional Ingredients

The dispersion of the invention contains the usual additional ingredients in quantities of 90–1 wt. % relative to polymer mixture A consisting of components (a) and (b). Quantities used and application of the customary additional ingredients in drug coatings are familiar to one of skill in the art. Customary additional ingredients include, for example, softeners, antiblocking agents, pigments, stabilizers, antioxidants, wetting agents, expanding agents, brighteners, aromatic substances or flavorings. They serve primarily as processing aids, and should ensure a safe and reproducible production method, as well as good long-term storage stability. They are added to the liquid polymer formulations before processing and can influence the permeability of the coatings, a characteristic that can be exploited, if desired, as an additional control parameter.

Softeners

Substances suitable as softeners generally have a molecular weight ranging from 100–2,000, and contain one or more hydrophilic groups in the molecule, for example, hydroxyl, ester, or amino groups. Suitable examples of softeners include citric acid alkyl ester, glycerin ester, phthalic acid alkyl ester, sebacic acid alkyl ester, sucrose ester, sorbitan ester, dibutyl sebacate, and polyethylene glycols 200–2,000. Preferred softeners include triethyl citrate and acetyl triethyl citrate. Esters that generally are liquid at room temperature, such as citrates, phthalates, sebacates, or castor oil, may also be mentioned.

Customary quantities of softeners used in the coatings and binders of the invention range from 5–30 wt. % relative to the polymer.

Antiblocking Agents

These substances, which generally have lipophilic properties are added to the spray suspensions and prevent an agglomeration of the cores during the film coating process. Preferred are talc, Mg or Ca stearate, powdered silicic acid, kaolin and nonionic emulsifiers having an HLB value ranging from 3–8. The usual quantities used for antiblocking agents in the coatings and binders of the invention range from 0–50 wt. % relative to the polymer.

Pigments

The addition is only rarely made in the form of a soluble dye. Generally, aluminum or iron oxide pigments are dispersed in a medium. Titanium dioxide is used as a white pigment. Quantities normally used in the coatings and binders of the invention range from 20–60 wt. % relative to the polymer mixture. Because of the high pigment binding ability, however, quantities of up to 80 wt. % can also be processed.

Aside from whiteners, antiblocking agents and pigments, stabilizers, antioxidants, wetting agents, expanding agents, brighteners, aromas and flavoring agents can be named as other substances that are customarily added and known to one of skill in the art.

Application as a Binder

Application as a binder is made by spraying the dispersion onto cores that have no active ingredients (nonpareils) with the simultaneous addition of powdered active ingredients or their mixtures. Furthermore, a dispersion that contains active ingredients can also be processed into a film so that a sheet-like pharmaceutical form is produced.

Another embodiment is the spraying of the dispersion together with the active ingredients dissolved or suspended in it.

Application as Coating

Core

Carriers for coatings include capsules, tablets, granulates, pellets and crystals of regular or irregular shape. The size of granulates, pellets, or crystals ranges from 0.01–2.5 mm, that of tablets from 2.5–30.0 mm. Capsules consist of gelatins, starches and cellulose derivatives.

They generally contain the biologically active substance (active ingredient) in an amount of up to 95%, as well as other inactive pharmaceutical ingredients up to 99.9 wt. %.

Customary production methods include direct pressing, pressing of dry, wet, or sintered granulates, extrusion and subsequent rounding, wet or dry granulation and direct pelletizing (for example, on plates), or by binding of powders (powder layering) to spheres (nonpareils) or particles that contain an active ingredient.

Aside from the active ingredient, they may contain other inactive pharmaceutical ingredients including binders such as cellulose and its derivatives, polyvinylpyrrolidone (PVP), humectants, disintegration accelerators, lubricants, disintigrants, (meth)acrylates, starch and its derivatives, sugar solubilizing agents and the like.

Of particular significance is the disintegration time of the core, which influences the release of the active ingredient. Today, short disintegration times of less than 5 or less than 10 min in the disintegration test according to the European Pharmacopoeia are desirable. Longer disintegration times are problematic because additional coatings further delay the release of the active ingredient and can jeopardize the therapeutic effect. At present, a disintegration time of 30 min is regarded as the limiting value. A small effect on the pH of the disintegration medium is advantageous. Therefore, tests are done in water and artificial gastric juice (0.1N HCl).

Incorporated pharmaceutical substances can elicit an uneven coloring or unpleasant, bitter taste. In order to improve the patient acceptance of such products, taste insulation for at least 30 sec is targeted (see Examples 9 and 16 in this regard).

The cores employed are homogeneous or have a layered construction. If engravings are made in the surface, they should as much as possible be only lightly covered by coatings.

Coatings

The layer thickness of the applied polymer mixtures of the invention varies greatly and depends on the processing method or the quantity of additional substances. The thickness ranges from 1–100 μm, preferably from 10–50 μm. On customary tablets, this corresponds to a polymer application of 0.5–5 wt. %.

The function of the polymer mixture in the final pharmaceutical product can be multifaceted:

protection from harmful environmental effects of moisture, gases, light, and the like.

odor or taste insulation identification by color mechanical stabilization insulation from intolerable ingredients avoidance of adhesion to the mucous membranes.

The low viscosity of the polymer mixture in the aqueous dispersion, even with high portions of solid substances up to 30%, is also advantageous, because engravings on the surface of tablets can be reproduced in detail.

Especially advantageous is the good protective and insulating effect of the polymer mixture of the invention with a simultaneously small effect on the disintegration of the tablets. Especially in comparison to simple coatings with HPMC, taste insulation of more than 30 sec can be achieved even with minimal polymer applications of 1 wt. %. Although thicker coatings improve disguising of the taste, they extend the disintegration time.

Also advantageous is the reliable covering of dye cores by coatings with a high pigment content. A special embodiment shape is the encapsulation of a second active ingredient into the coating on a core that contains active ingredient.

Application of the Film Coating

The method of application of the dispersion is by casting, painting, or spray application from an aqueous dispersion, by suspension, by liquification, or by direct application of powder. In the process, it is critical to the embodiment that regular, closed coatings are produced.

For the method of application by state of the state of the art procedures see, for example, Bauer, Lehmann, Osterwald, Rothgang, "Coated drugs," Wissenschaftliche Verlagsgesellschaft mbH, Stuttgart, Chapter 7, pp. 165–196.

For the properties relevant to the application, required tests and specifications are listed in pharmacopoeia.

Details can be found in the current textbooks, for example:

R. Voigt (1984): Lehrbuch der pharmazeutischen Technologie [Textbook of pharmaceutical technology]; Verlag Chemie, Weinheim Beerfield Beach/Fla.—Basel.

H. Sucker, P. Fuchs, P. Speiser: Pharmazeutische Technologie [Pharmaceutical technology], Georg Thieme Verlag Stuttgart (1991), especially Chapters 15 and 16, pp. 626–642.

A. R. Gennaro (Editor), Remington's Pharmaceutical Sciences, Mack Publishing Co., Easton, Pa. (1985), Chapter 88, pp. 1567–1573.

P. H. List (1982): Arzneiformenlehre [Science of drugs], Wissenschaftliche Verlagsgesellschaft mbH, Stuttgart.

Biologically Active Substances (or Active Pharmaceutical Substances)

Biologically active substances (or active pharmaceutical substances) which can be formulated with the present coating material are those which are intended to be applied to or in the human or animal body, in order to:

1. cure, alleviate, prevent, or diagnose diseases, pain, physical injuries, or ailments.

2. to aid in determining the quality, condition, or functions of the body or mental conditions.

3. to replace active ingredients or bodily fluids generated by the human or animal body.

4. to combat, eliminate or render harmless agents of disease, parasites, or substances foreign to the body or 5. to influence the quality, condition, or functions of the body or mental conditions.

Conventional pharmaceutical substances can be found in reference books, such as the Red List or Merck Index.

According to the invention, all active ingredients can be used that fulfill the desired therapeutic effect in the sense of the above definition, and have sufficient thermal stability.

Important examples (groups and individual substances) without claiming to be comprehensive are the following:

analgesics antiallergy and antiarrhythmic drugs antibiotics, chemotherapeutics, antidiabetics, antidotes, antiepileptics, antihypertensives, antihypotensives, anticoagulants, antimycotics, antiphlogistics, beta blockers, calcium antagonists, and ACE inhibitors, broncholytics/antiasthmatics, cholinergics, corticosteroids (internal)

dermatics, diuretics, enzyme inhibitors, enzyme preparations and transport proteins expectorants, geriatric agents, antipodagrics, flu remedies, hormones and their inhibitors, hypnotics/sedatives, cardiac drugs, lipid reducing agents parathyroid hormones/calcium metabolism regulators, psychopharmaceuticals, sexual hormones and their inhibitors, spasmolytics, sympatholytics, sympathomimetics, vitamins, wound treatment agents, cytostatics.

Preferred active ingredients for delayed release of active ingredients include:

Nifedipine, diltiazem, theophylline, diclofenac sodium, ketoprofen, ibuprofen, indomethacin, ambroxol, terbutaline, vincamine, propranolol, pentoxifylline, codeine, morphine, etilefrin, carbamazepine, and their salts that are used in therapy.

Application Forms

Fundamentally, the described drugs can be administered directly by oral application. The granular powders, pellets, or particles produced according to the invention may be filled into gelatin capsules, bags (sachets), or suitable multidose containers with a dosing device. Intake is in solid form or as liquid suspensions.

Through compression with or after the admixture of other inactive ingredients, tablets are obtained that disintegrate after intake and release the subunits that usually are coated. Also conceivable is the encapsulation of agglomerates in polyethylene glycol or lipids for the production of suppositories or vaginal drugs.

Coated tablets are packed in blister or multiple-dose containers and removed by the patient directly before intake.

Having now generally described the invention, a further understanding can be obtained by reference to certain specific examples which are provided herein for purpose of illustration only and are not intended to be limiting unless otherwise specified.

EXAMPLES

Examples 1–24 are summarized in the following tables; components (a) and (b) correspond to (a) and (b) in claim 1. Examples 16–20 are Comparative Examples, which are not within the scope of the invention.

Abbreviations Employed in Table 1 Below are as Follows

PM1=polymethacrylate copolymer consisting of 10 wt. % trimethylammonium ethyl methacrylate chloride, 60 wt. % methyl methacrylate, and 30 wt. % ethyl acrylate PM2=copolymer consisting of 5 wt. % trimethylammonium methyl methacrylate chloride, 65 wt. % methyl methacrylate, and 30 wt. % ethyl acrylate PM3=copolymer consisting of 30 wt. % ethyl acrylate, and 70 wt. % methyl methacrylate.

Na-CMC type 1=sodium carboxymethylcellulose with a molecular weight (Mw) of approximately 50,000, degree of substitution: 0.65–0.90, alkali content (%) Na: 7.0–8.9, 2% viscosity in water at 20° C.: 25–50 mPas.

Na-CMC type 2=sodium carboxymethylcellulose with a molecular weight (Mw) of approximately 20,000, degree of substitution: 0.7, alkali content (%) Na: 7.0, 2% viscosity in water at 20° C.: 2–3 mPas.

Na-CMC type 3=sodium carboxymethylcellulose with a molecular weight (Mw) of approximately 65,000, degree of substitution: 0.6–0.8, alkali content (%) Na: <9.7, 2% viscosity in water at 20° C.: 25–32 mPas.

Na-CMC type 4=sodium carboxymethyl cellulose with a molecular weight (Mw) of approximately 250,000, degree of substitution: 0.65–0.9, alkali content (%) Na: 7.0–8.9, 2% viscosity in water at 25° C.: 400–600 mPas.

HPMC=hydroxylpropylmethylcellulose (Methocelo® E 5)

TABLE 1

| Example | (a) | (b) | | Key word |
|---|---|---|---|---|
| 1 | PM 1 | 5% | Na-CMC Type 1 | Disintegration time <20 min |
| 2 | PM 1 | 7% | Na-CMC Type 1 | Disintegration time <20 min |
| 3 | PM 1 | 15% | Na-CMC Type 1 | Disintegration time <20 min |
| 4 | PM 1 | 20% | Na-CMC Type 1 | Disintegration time <20 min |
| 5 | PM 1 | 5% | Na-CMC Type 2 | Disintegration time <20 min |
| 6 | PM 1 | 5% | Na-CMC Type 3 | Disintegration time <20 min |
| 7 | PM 2 | 10% | Na-CMC Type 1 | Disintegration time <20 min |
| 8 | PM 1 | 20% | Na-CMC Type 1 | Pigment binding ability |
| 9 | PM 1 | 9.7% | Na-CMC Type 1 | Taste insulation |
| 10 | PM 1 | 9.7% | Na-CMC Type 1 | Abrasion |
| 11 | PM 1 | 10% | Na-CMC Type 1 | Particle covering |
| 12 | PM 1 | 8.3% | Na-CMC Type 1 | Release behavior |
| 13 | PM 1 | 10% | Na-CMC Type 1 | Spray drying |
| 14 | PM 1 | 10% | Na-CMC Type 1 | Production in the melted state |
| 15 | PM 1 | 10% | Na-CMC Type 1 | Production in suspension |
| 16 | — | 100% | HPMC | Taste insulation |
| 17 | PM 1 | 11% | Xanthan | Disintegration time > 30 min |
| 18 | PM 3 | 10% | Na-CMC Type 1 | Disintegration time > 30 min |
| 19 | PM 2 | 10% | Na-CMC Type 1 | Organic solution/ disintegration time |
| 20 | PM 1 | 11% | Na-CMC Type 4 | Na-CMC Mw = 250.000 |
| 21 | PM 1 | 10% | Na-CMC Type 1 | (from Example 13) chewable tablets |
| 22 | PM 1 | 10% | Na-CMC Type 1 | Release behavior |
| 23 | PM 1 | 10% | Na-CMC Type 1 | (from Example 13) disintegration time |
| 24 | PM 2 | 10% | Na-CMC Type 1 | Formation of film |

TABLE 2

| Ingredients | I Placebo tablets | II Placebo tablets | III Quinidine sulfate tablets | IV Placebo tablets with engraving | V Tablets | VI Hard gelatin capsules |
|---|---|---|---|---|---|---|
| Cellactose ™ | 94.5% | 83.3% | 92.5% | 94.5% | | |
| Avicel ™ PH 102 | 5.0% | 6.2% | 5.0% | 5.0% | | |
| Mg-Stearate | 0.5% | 0.5% | 0.5% | 0.5% | | |
| Quinidine sulfate | | | 2.0% | | | |
| Active ingredient | | | | | | ca. 90% |
| Disintegration accelerator, mold release agent | | | | | | ca. 10% |
| Acetyl salicylic acid | | | | | | 400 mg |

TABLE 3

|  | I<br>Placebo tablets | II<br>Placebo tablets | III<br>Quinidine sulfate<br>tablets | IV<br>Placebo tablets<br>with engraving | V<br>Tablets | VI<br>Hard gelatin<br>capsules |
|---|---|---|---|---|---|---|
| Appearance | White | White | White | White | Dark brown | Red/green |
| Diameter | 10.0 mm | 10.0 mm | 10.03 mm | 10.0 mm | 12 mm | 6.3 mm |
| Height | 4.0 mm | 4.1 mm | 3.91 mm | 3.59 mm | 5.5 mm |  |
| Length |  |  |  |  |  | 19.6 mm |
| Weight | 299.3 mg<br>(291–306 mg) | 306.3 mg<br>(294–311 mg) | 304.6 mg<br>(398–312 mg) | 310 mg | ~600 mg | 487 mg |
| Hardness | 52–74 N | 53–75 N | 120.4 N<br>(113–133 N) | 119 N | 60–70 N |  |
| Disintegration in demineralized water | 10–20 min. | 4–14 min | 13–20 min | ~12 min | 24–28 min | 2–4 min |
| Disintegration in 0.1N HCl | 6–12 min | 4–8 min | 14–20 min | ~14 min |  | 2–4 min |

1. Protective Coating on Tablets: (5% Na-CMC Type 1)

9 g talc, 4 g triethyl citrate, and 0.9 g Na-CMC Type 1 are mixed with 86 g water in a beaker, and evenly dispersed by means of Ultra Turrax T 50 deflocculating agent (Jahnke and Kunkel Co.). Subsequently, the suspension is slowly poured into 60 g of a 30% dispersion of PM1 (Eudragit RL 30 D), which has been placed in a stainless steel container, and mixed with regular stirring. This spray suspension is applied to 1000 g of tablets as shown in column I in Table 2 above in a coating pan by means of a spray gun (spray pressure 0.8 bar) over a period of 23 min. The total application totals 2.0 mg polymer consisting of EUDRAGIT RL 30 D per $cm^2$ tablet surface. During the application procedure, partial quantities with 1 and 1.5 mg polymer application/CM tablet surface are removed. All coated tablets are dried for 24 h at 40° C.

The coated tablets exhibit a smooth and even surface and disintegrate in the disintegration test according to the European Pharmacopoeia in purified water and artificial gastric juice within the following times (Table 4):

TABLE 4

| Polymer application | | | |
|---|---|---|---|
| Medium | 1 mg | 1.5 mg | 2 mg |
| Demineralized water | 13–15 min | 14–18 min | 15–18 min |
| 0.1N HCl | 14–18 min | 15–19 min | 14–20 min |

2. Protective Coating on Tablets: (10% Na-CMC Type 1

14 g talc, 6 g triethyl citrate, and 2.8 g Na-CMC Type 1 are mixed with 139 g water in a beaker, and evenly dispersed by means of Ultra Turrax T 50 deflocculating agent (Jahnke and Kunkel Co.). Subsequently, the suspension is slowly poured into 93 g of a 30% dispersion of polymer PM1 which has been placed in a stainless steel container, and mixed with stirring. This spray suspension is applied to 1500 g of tablets according to column II in Table 2 in a coating pan by means of a spray gun (spray pressure 0.8 bar) over a period of 42 min. The application totals 2.0 mg polymer PM 1 per $cm^2$ tablet surface. During the process of application, partial quantities at 1 and 1.5 mg polymer application/$cm^2$ tablet surface are removed. All coated tablets are dried for 24 hr at 40° C. The coated tablets exhibit a smooth and even surface and disintegrate in the disintegration test according to the European Pharmacopoeia in purified water and artificial gastric juice within the times shown in following Table 5:

TABLE 5

| Polymer application | | | |
|---|---|---|---|
| Medium | 1 mg | 1.5 mg | 2 mg |
| Demineralized water | 5–10 min | 4–10 min | 6–8 min |
| 0.1N HCl | 4–8 min | 4–7 min | 5–8 min |

3. Protective Coating on Tablets: (15% Na-CMC Type 1)

9 g talc, 4 g triethyl citrate, and 2.7 g Na-CMC Type 1 are mixed with 94 g water in a beaker, and evenly dispersed by means of Ultra Turrax T 50 deflocculating agent (Jahnke and Kunkel Co.). Subsequently, the suspension is slowly poured into 60 g of a 30% dispersion of polymer PM1 that has been put in a stainless steel container, and mixed with regular stirring. This spray suspension is applied to 1000 g of tablets according to column I in Table 2 above in a coating pan by means of a spray gun (spray pressure 0.8 bar) over a period of 33 min. The total application totals 2.0 mg polymer PM1 per $cm^2$ tablet surface. During the application procedure, partial quantities with 1 and 1.5 mg polymer application/$cm^2$ tablet surface are removed. All coated tablets are dried for 24 h at 40° C.

The coated tablets exhibit a smooth and even surface and disintegrate in the disintegration test according to the European Pharmacopoeia in purified water and artificial gastric juice within the times shown in following Table 6:

TABLE 6

| Polymer application | | | |
|---|---|---|---|
| Medium | 1 mg | 1.5 mg | 2 mg |
| Demineralized water | 15–19 min | 16–20 min | 15–19 min |
| 0.1N HCl | 14–19 min | 13–19 min | 14–21 min |

4. Protective Coating on Tablets: (20% Na-CMC Type 1)

9 g talc, 4 g triethyl citrate, and 3.6 g Na-CMC Type 1 are mixed with 98 g water in a beaker, and evenly dispersed by means of Ultra Turrax T 50 deflocculating agent (Jahnke and Kunkel Co.). Subsequently, the suspension is slowly poured into 60 g of a 30% dispersion of polymer PM1 that has been put in a stainless steel container, and mixed with regular stirring. This spray suspension is applied to 1000 g of tablets according to column I in Table 2 in a coating pan by means of a spray gun (spray pressure 0.8 bar) over a period of 33 min. The total application totals 2.0 mg polymer PM1 per $cm^2$ tablet surface. During the application process, partial quantities with 1 and 1.5 mg polymer application/$cm^2$ tablet surface are removed. All coated tablets are dried for 24 h at 40° C.

The coated tablets exhibit a smooth and even surface and disintegrate in the disintegration test according to the European Pharmacopoeia in purified water and artificial gastric juice within the times shown in following Table 7:

TABLE 7

| | Polymer application | | |
|---|---|---|---|
| Medium | 1 mg | 1.5 mg | 2 mg |
| Demineralized water | 12–18 min | 14–19 min | 15–22 min |
| 0.1N HCl | 11–17 min | 12–16 min | 13–19 min |

5. Protective Coating on Tablets: (Na-CMC Type 2)

9 g talc, 4 g triethyl citrate, and 2 g Na-CMC Type 2 are mixed with 90 g water in a beaker, and evenly dispersed by means of Ultra Turrax T 50 deflocculating agent (Jahnke and Kunkel Co.). Subsequently, the suspension is slowly poured into 60 g of a 30% dispersion of polymer PM1 which has been placed in a stainless steel container, and mixed with stirring. This spray suspension is applied to 1000 g of tablets according to column I in Table 2 in a coating pan by means of a spray gun (spray pressure 0.8 bar) over a period of 30 min. The total application totals 2.0 mg PM1 per $cm^2$ tablet surface. During the application process, partial quantities with 1 and 1.5 mg polymer application/$cm^2$ tablet surface are removed. All coated tablets are dried for 24 h at 40° C.

The coated tablets exhibit a smooth and even surface and disintegrate in the disintegration test according to the European Pharmacopoeia in purified water and artificial gastric juice within the times shown in following Table 8:

TABLE 8

| | Polymer application | | |
|---|---|---|---|
| Medium | 1 mg | 1.5 mg | 2 mg |
| Demineralized water | 16 min | 17 min | 18 min |
| 0.1N HCl | 16 min | 16 min | 19 min |

6. Protective Coating on Tablets: (Na-CMC Type 3)

13.8 g talc, 5.5 g triethyl citrate, and 2.8 9 Na-CMC Type 3 are mixed with 134.2 g water in a beaker, and evenly dispersed by means of Ultra Turrax T 50 deflocculating agent (Jahnke and Kunkel Co.). Subsequently, the suspension is slowly poured into 92 g of a 30% dispersion of polymer PM1 which has been placed in a stainless steel container, and mixed with stirring. This spray suspension is applied to 1500 g of tablets according to column I in Table 2 in a coating pan by means of a spray gun (spray pressure 0.8 bar) over a period of 27 min. The total application totals 2.0 mg polymer per $cm^2$ tablet surface. During the application procedure, partial quantities with 1 and 1.4 mg polymer application/$cm^2$ tablet surface are removed. All coated tablets are dried for 24 hr at 40° C.

The coated tablets exhibit a smooth and even surface and disintegrate in the disintegration test according to the European Pharmacopoeia in purified water and artificial gastric juice within the times shown in the following Table 9:

TABLE 9

| | Polymer application | | |
|---|---|---|---|
| Medium | 1 mg | 1.5 mg | 2 mg |
| Demineralized water | 15–17 min | 14–17 min | 16–20 min |
| 0.1N HCl | 15–19 min | 18–20 min | 17–24 min |

7. Protective Coating on Tablets 9 g talc, 4 g triethyl citrate, and 1.8 g Na-CMC Type 1 are mixed with 90 g water in a beaker, and evenly dispersed by means of Ultra Turrax T 50 deflocculating agent (Jahnke and Kunkel Co.). Subsequently, the suspension is slowly poured in 60 g of a 30% dispersion of polymer PM2 that has been put into a stainless steel container, and mixed with regular stirring. This spray suspension is applied to 1000 g of tablets according to column I in Table 2 in a coating pan by means of a spray gun (spray pressure 0.9 bar) over a period of 26 min. The total application totals 2.0 mg polymer PM2 per $cm^2$ tablet surface. During the application process, partial quantities with 1 and 1.5 mg polymer application/$cm^2$ tablet surface are removed. All coated tablets are dried for 24 h at 40° C.

The coated tablets exhibit a smooth and even surface and disintegrate in the disintegration test according to the European Pharmacopoeia in purified water and artificial gastric juice within the times in following Table 10:

TABLE 10

| | Polymer application | | |
|---|---|---|---|
| Medium | 1 mg | 1.5 mg | 2 mg |
| Demineralized water | 16 min | 17 min | 17 min |
| 0.1N HCl | 18 min | 18 min | 19 min |

8. Colored Coating on Tablets 66 g talc, 5 g triethyl citrate, and 102 g of a 33% polyethylene glycol 6000 solution in water, 118 g titanium dioxide, and 3 g quinoline gel black E 104 are mixed with 548 g water in a beaker, and evenly dispersed by means of Ultra Turrax T 50 deflocculating agent (Jahnke and Kunkel Co.). Subsequently, 83 g of a 30% dispersion of polymer PM1 are put in a stainless steel container, and with stirring, 3 g of a 33% Tween 80 solution in water and 100 g of a 5% Na-CMC Type 1 solution in water are added. While stirring, the dispersed inactive ingredients are added.

This spray suspension is applied to 2500 g of dark-colored tablets according to column V in Table 2 in a coating pan by means of a spray gun (spray pressure 1 bar) over a period of 81 min. The total application totals 1.4 mg polymer PM1 per $cm^2$ tablet surface. During the application procedure, partial quantities with 1 and 1.5 mg polymer application/$cm^2$ tablet surface are removed. All coated tablets are dried for 17 h at 40° C.

The tablets exhibit a smooth and even yellow surface and disintegrate in the disintegration test according to the European Pharmacopoeia in purified water after 22–35 min:

9. Taste Insulation 21 g talc and 8 g triethyl citrate are mixed with 128 g water in a beaker and evenly dispersed by means of Ultra Turrax T 50 deflocculating agent (Jahnke and Kunkel Co.). Subsequently, the suspension is slowly poured into a mixture of 137 g of a 30% dispersion of polymer PM1, 6 g of a 33% Tween 80 solution in water, and 80 g of a 5% Na-CMC Type 1 solution in water which has been placed in a stainless steel container and the batch is mixed with regular stirring. This spray suspension is applied to 1500 g of tablets according to column III in the table in a coating pan by means of a spray gun (spray pressure 0.8 bar) over a period of 72 min. The total application totals 3.0 mg polymer PM1 per $cm^2$ tablet surface. During the application procedure, partial quantities with 1.0, 1.5, 2.0, and 2.5 mg polymer application/$cm^2$ tablet surface are removed. All coated tablets are dried for 24 h at 40° C. The tablets with a polymer application of 3 mg/$cm^2$ disintegrate in the disintegration test according to the European Pharmacopoeia in purified water and artificial gastric juice after 18–30 min.

The masking of the bitter-tasting active ingredient in the tablets was determined by 4 test subjects (mean values) as shown in Table 11:

TABLE 11

| Polymer application | 1.0 mg | 1.5 mg | 2.0 mg | 2.5 mg |
|---|---|---|---|---|
| Uncoated | | | | |
| Masking of taste (seconds) 0 | 55 | 127 | 173 | >180 |

10. Stabilization of the Surface (Abrasion)

21 g talc and 8 g triethyl citrate are mixed with 128 g water in a beaker and evenly dispersed by means of Ultra Turrax T 50 deflocculating agent (Jahnke and Kunkel Co.). Subsequently, the suspension is slowly poured into a mixture of 137 g of a 30% dispersion of polymer PM1, 6 g of a 33% Tween 80 solution in water, and 80 g of a 5% NA-CMC Type 1 solution in water that has been put in a stainless steel container and the batch is mixed with regular stirring. This spray suspension is applied to 1500 g of tablets according to III in the table in a coating pan by means of a spray gun (spray pressure 0.8 bar) over a period of 72 min. The total application totals 3.0 mg polymer per $cm^2$ tablet surface. The coated tablets are dried for 24 h at 40° C. In the friability test according to USP 23, the tablets exhibit the values as shown in following Table 12:

TABLE 12

| | Friability |
|---|---|
| Uncoated | 0.04% |
| Coated | 0.02% |

11. Protective Coating on Particles in a Fluidized Bed Device 25 g talc and 10 g triethyl citrate are mixed with 61 g water in a beaker and evenly dispersed by means of an Ultra Turrax T 50 deflocculating agent (Jahnke and Kunkel Co.). Subsequently, the suspension is slowly poured into a mixture of 167 g of a 30% dispersion of polymer PM1, 8 g of a 33% Tween 80 solution in water, and 100 g of a 5% Na-CMC Type 1 solution in water, which has been placed in a stainless steel container, and the batch is mixed with stirring.

This spray suspension is applied to 1000 g potassium chloride crystals (particle size 0.3–1 mm) in a fluidized bed device Glatt GPCG 1 by means of a spray gun (spray pressure 2 bar) over a period of 63 min. The total application amounts to 5% polymer PM1. The coated crystals are dried over 24 h at 40° C. The coated crystals mask the taste for approximately 5 sec, and in the release test analogous to USP 23 paddle device in water, exhibit the values shown in Table 13:

TABLE 13

| Time (min) | 10 | 20 | 30 |
|---|---|---|---|
| Crystals of active ingredient | 97.4% | 97.4% | 97.4% |

Coating on Capsules 12 g talc and 5 g triethyl citrate are mixed with 80 g water in a beaker and evenly dispersed by means of Ultra Turrax T 50 deflocculating agent (Jahnke and Kunkel Co.). Subsequently, the suspension is slowly poured into a mixture of 80 g of a 30% dispersion of polymer PM1, 3 g of a 33% Tween 80 solution in water, and 40 g of a 5% Na-CMC Type 1 solution in water, which has been placed in a stainless steel container, and the batch is mixed with stirring.

This spray suspension is applied to 1000 g hard gelatin capsules according to column VI in Table 2 in a coating pan by means of a spray gun (spray pressure 0.8 bar) over a period of 47 min. The total application amounts to 3.0 mg polymer PM1 per $cm^2$ capsule surface. The coated capsules are dried over 24 hr at 40° C. The capsules with a polymer application of 3 $mg/cm^2$ disintegrate in the disintegration test according to the European Pharmacopoeia in purified water and artificial gastric juice after 9–15 min.

In the release test according to USP 23 rotating basket method in 0.1N HCl, the capsules exhibit the values shown in following Table 14:

TABLE 14

| Time (min) | 30 | 60 | 90 | 120 |
|---|---|---|---|---|
| Polymer application ($mg/cm^2$) | | | | |
| 1.2 | 2.8% | 31.5% | 39.6% | 43.2% |
| 1.5 | 1.6% | 16.0% | 21.5% | 26.4% |
| 2.2 | 1.9% | 5.1% | 9.8% | 13.7% |
| 3 | 1.7% | 4.3% | 6.7% | 9.1% |

13. Production of a Spray-dried Polymer Mixture 12154 g of a 30% dispersion of polymer PM1 are placed in a stainless steel container and stirred evenly with an electric stirrer. By means of a hose pump, a mixture of 7293 g of a 5% aqueous solution of Na-CMC Type 1 and 553 g of a 33% aqueous solution of Tween 80 are slowly metered in. The resulting mixture is dried by conventional spray-drying technology. The resulting powder is free-flowing and can be redispersed in demineralized water.

14. Production of the Polymer Mixture by Melting

In a stainless steel container, 100 g of polymer PM1 in powder form, 10 g Na-CMC Type 1, and 40 g triethyl citrate are mixed and homogeneously melted in a drying chamber at 120° C. The mixture was comminuted after cooling by means of an IKA analytical mill. 23 g of the milled material are mixed with 207 g water and stirred for 24 h at 20° C. with a magnetic stirrer. The suspension is dried in a drying chamber in a flat dish at 40° C. A homogeneous, cohesive, elastic film is produced.

15. Production of the Polymer Mixture by Direct Suspension (Mixing) of the Powder 50 g polymer PM1 in powder form and 5 g Na-CMC Type 1 are stirred in 450 g water by means of a magnetic stirrer. Subsequently, 10 g triethyl citrate are added and stirred for another 60 min. The suspension is dried in a drying chamber in a flat dish at 40° C. A homogeneous, cohesive, elastic film is produced.

16. (Comparative Example): Taste Insulation with Hydroxypropylmethylcellulose

In a beaker, 41 g of hydroxypropylmethylcellulose (HPMC) are dissolved in 200 g water heated to 60° C. 2 g talc and 4 g polyethylene glycol 6000 are mixed with 145 g water and evenly dispersed by means of Ultra Turrax T 50 deflocculating agent (Jahnke and Kunkel Co.). Subsequently, the suspension is slowly poured into the HPMC solution. This spray suspension is applied to 1500 g tablets according to column III in Table 2 by means of a spray gun (spray pressure 2.5 bar) over a period of 98 min. The total application amounts to 3.0 mg HPMC per $cm^2$ tablet surface. During the application procedure, partial quantities with 1.0, 1.5, 2.0, and 2.5 mg polymer application/ $cm^2$ tablet surface are removed. All coated tablets are dried for 24 h at 40° C. The masking of the bitter tasting active ingredient in the tablets is determined by 4 test subjects (mean values) as shown in Table 15:

TABLE 15

| Polymer application | 1.0 mg | 1.5 mg | 2.0 mg | 2.5 mg | 3.0 mg |
|---|---|---|---|---|---|
| Uncoated Taste insulation (sec) | 0 | 8 | 15 | 17 | 21 |

17. (Comparative Example): Coating with Xanthan 9 g talc, 4 g triethyl citrate, and 400 g of a 0.5% aqueous solution of xanthan gum are mixed with 77 g water in a beaker and evenly dispersed by means of Ultra Turrax T 50 deflocculating agent (Jahnke and Kunkel Co.). Subsequently, the suspension is slowly poured into 60 g of a 30% dispersion of PM1 which has been placed in a stainless steel container, and the batch is mixed with stirring.

This spray suspension is applied to 1000 g tablets according to column I in Table 2 in a coating pan by means of a spray gun (spray pressure 0.9 bar) over a period of 70 min. The total application amounts to 2.0 mg polymer PM1 per $cm^2$ tablet surface. During the application procedure, partial quantities of 1 and 1.5 mg polymer application/$cm^2$ tablet surface are removed. All coated tablets are dried over 24 h at 40° C.

The coated tablets exhibit a smooth and even surface, and disintegrate in the disintegration test according to the European Pharmacopoeia in purified water and artificial gastric juice after the times shown in Table 16:

TABLE 16

| | Polymer application | | |
|---|---|---|---|
| Medium | 1 mg | 1.5 mg | 2 mg |
| Demineralized water | 18 min | >30 min | >30 min |
| 0.1N HCl | 23 min | >30 min | >30 min |

18. (Comparative Example): Coating with a Polymethacrylate Dispersion Not According to the Invention 13.8 g talc and 56 g of a 5% aqueous solution of Na-CMC Type 1 are mixed with 59 g water in a beaker and evenly dispersed by means of Ultra Turrax T 50 deflocculating agent (Jahnke and Kunkel Co.). Subsequently, the suspension is poured slowly in 92 g of a 30% aqueous dispersion of polymer PM3 which has been placed into a stainless steal container, and the batch is mixed under regular stirring.

This spray suspension is applied to 1500 g of tablets according to column I in Table 2 in a coating pan by means of a spray gun (spray pressure 0.8 bar) over a period of 60 min. The total application totals 2.0 mg polymer consisting of EUDRAGIT NE 30 D per $cm^2$ tablet surface. During the application procedure, partial quantities with 1 and 1.5 mg polymer application/$cm^2$ tablet surface are removed. All coated tablets are dried for 24 h at 40° C.

The coated tablets exhibit a smooth and even surface and disintegrate in the disintegration test according to the European Pharmacopoeia in purified water and artificial gastric juice within the times shown in Table 17:

TABLE 17

| | Polymer application | | |
|---|---|---|---|
| Medium | 1 mg | 1.5 mg | 2 mg |
| Demineralized water | 24 −> 30 min | 28 −> 30 min | >30 min |
| 0.1N HCl | 29 −> 30 min | >30 min | >30 min |

19. (Comparative Example): Coating of Organic Solution

In a beaker, 11 g granular powder of polymer PM1, 5.5 g talc, 2.2 g triethyl citrate, and 1.1 g Na-CMC Type 1 dissolved in 11.3 g water are mixed with 215.7 g ethanol, and dispersed by means of Ultra Turrax T 50 deflocculating agent (Jahnke and Kunkel Co.)

This spray suspension is applied to 600 g of tablets according to column I in Table 18 in a coating pan by means of a spray gun (spray pressure 0.6 bar) over a period of 26 min. The total application totals 2.0 mg polymer PM1 per $cm^2$ tablet surface.

During the application procedure, partial quantities with 1 and 1.5 mg polymer application/$cm^2$ tablet surface are removed. All coated tablets are dried for 2 hr at 40° C. The coated tablets exhibit a smooth and even surface and disintegrate in the disintegration test according to the European Pharmacopoeia in purified water and artificial gastric juice within the times shown in following Table 18:

TABLE 18

| | Polymer application | | |
|---|---|---|---|
| Medium | 1 mg | 1.5 mg | 2 mg |
| Demineralized water | 17–26 min | 22–27 min | >30 min |
| 0.1N HCl | 16–25 min | >30 min | >30 min |

20. (Comparative Example) NA-CMC with too High a Molecular Weight

Protective coating on tablets: 9 g talc, 4 g triethyl citrate, and 2 g Na-CMC Type 4-with a molecular weight of approximately 250,000, and 90 g water are mixed in a beaker, and evenly dispersed by means of Ultra Turrax T 50 deflocculating agent (Jahnke and Kunkel Co.). Subsequently, the suspension is slowly poured in 60 g of a 30% aqueous dispersion of polymer PM1 which has been placed into a stainless steel container, and the batch is mixed under stirring. A viscous, semifluid mass is formed that cannot be processed by conventional spray application.

21. Chewable Tablets Consisting of Coated Crystals 346 g of coated potassium chloride crystals according to Example 11 are mixed with 75 g Avicel PH, 102.75 g corn starch, 2.5 g Aerosil 200, and 1.5 g magnesium stearate in an eccentric tumbler, and then pressed into tablets using an eccentric press (Korsch EK 0 Typee) with the following galenic data: diameter 10 mm, weight 375 mg, breaking strength 20–30N, disintegration in demineralized water and 0.1N HCl<30 sec. The resulting tablets have a taste masking, when chewed, of approximately 10 sec, and in the release test analogous to USP 23 paddle device in water, exhibit the values shown in following Table 19:

TABLE 19

| Time (min): | 10 | 20 | 30 |
|---|---|---|---|
| Crystals of active ingredient, coated | 97.4% | 97.4% | 97.4% |
| Tablets of active ingredient | 96.7% | 96.7% | 96.7% |

22. Quickly Disintegrating Active Ingredient Tablets Consisting of Wet Granules 1000 g triameteren powder and 1000 g lactose EPD 80 are placed in a Stephan UM 12 positive mixer, and granulated with a mixture of 333 g of a 30% dispersion of polymer PM1 and 10 Na-CMC Type 1 dissolved in 190 g water at 2000 rpm. This mixture is then dried for 24 hr at 40° C. in a drying chamber and passed through a 1.0-mm sieve.

2000 g of the active ingredient granulate produced in this way are mixed with 20 crosspovidone XL and 10 g magnesium stearate in a double-cone mixer and by means of a Korsch EK 0 eccentric press at 10 kN pressing force, pressed into tablets measuring 10 mm in diameter and weighing 306 mg. In the release test analogous to USP 23 paddle device in 0.1N HCl, the tablets produced in this way exhibit the values shown in following Table 20:

TABLE 20

| Time (min): | 15 | 30 | 45 | 60 |
|---|---|---|---|---|
| Active ingredient granulate | 72.2% | 87.7% | 94.0% | 96.6% |
| Active ingredient tablets | 49.1% | 83.7% | 95.5% | 98.8% |

23. Coating on Tablets Consisting of Redispersed Powder

In a beaker, 100 g of spray-dried product from Example 13 are dispersed in 233 g water by means of Ultra Turrax T 50 within 10 min. In a beaker, 13.8 g talc and 5.5 g triethyl citrate are mixed with 130 g water and evenly dispersed by means of Ultra Turrax T 50 deflocculating agent (Jahnke and Kunkel Co.). Subsequently, the suspension is slowly poured into 106.1 g of the redispersion produced previously, which has been placed in a stainless steel container, and the batch is mixed with stirring.

This spray suspension is applied to 1500 g of tablets according to column I in Table 2 in a coating pan by means of a spray gun (spray pressure 0.8 bar) over a period of 60 min. The total application totals 2.0 mg polymer PM1 per $cm^2$ tablet surface. During the application procedure, partial quantities with 1 and 1.5 mg polymer application/$cm^2$ tablet surface are removed. All coated tablets are dried for 24 hr at 40° C.

The coated tablets exhibit a smooth and even surface and disintegrate in the disintegration test according to the European Pharmacopoeia in purified water and artificial gastric juice within the times shown in following Table 21:

TABLE 21

| | Polymer application | | |
|---|---|---|---|
| Medium | 1 mg | 1.5 mg | 2 mg |
| Demineralized water | 17–22 min | 18–23 min | 18–21 min |
| 0.1 N HCl | 17–22 min | 15–19 min | 14–20 min |

24. Production of the Polymer Mixture with Spray-dried Polymer PM2

50 g powder from a spray-dried 30% aqueous dispersion of polymer PM2 are redispersed in 200 g water by means of a magnetic stirrer for 60 min, and subsequently 5 g Na-CMC Type 1 as well as 200 g water are stirred by means of a magnetic stirrer and mixed for another 2 h. Subsequently, 10 g triethyl citrate are added and stirred for another 15 min. The suspension is dried in a flat dish at 40° C. in a drying chamber. A homogeneous, cohesive, elastic film is formed.

The disclosure of German Priority application Serial No. 198 09 719.0 filed Mar. 6, 1998 is hereby incorporated by reference into the present application.

Obviously, numerous modifications and variations of the present invention are possible in light of the above teachings. It is, therefore, to be understood that within the scope of the appended claims, the invention may be practiced otherwise than as specifically described herein.

What is claimed as new and is intended to be secured by Letters Patent is:

1. An aqueous dispersion for the production of quickly disintegrating binders or coatings for solid oral drugs containing 90–40 wt. % water and 10–60 wt. % solids whereby said solids are composed of:
   (A) 10–99 wt. % of a polymer mixture consisting of;
      (a) 75–99 wt. % of a polymethacrylate copolymer consisting of 98–85 wt. % of alkyl(meth)acrylate monomers with $C_1$–$C_4$ alkyl residues and 2–15 wt. % of alkyl(meth)acrylate monomers with a quaternary ammonium group in the alkyl residue, and (b) 25–1 wt. % of an alkali salt of carboxymethylcellulose having a weight average molecular weight of less than 150,000, and
   (B) 90–1 wt. % of at least one pharmaceutically acceptable ingredient.

2. The aqueous dispersion according to claim 1, wherein said $C_{1-4}$ alkyl (meth)acrylate monomer is methyl acrylate, ethyl acrylate, butyl acrylate, butyl methacrylate or methyl methacrylate.

3. The aqueous dispersion according to claim 1, wherein said alkyl (meth)acrylate monomer with a quaternary ammonium group in the alkyl residue is acryl or methacryloxytrimethylammonium chloride or methosulfate, benzyldimethylammonium methyl methacrylate chloride, diethylmethylammonium ethyl acrylate or methacrylate methosulfate, N-trimethylammonium propyl methacrylamide chloride, N-trimethylammonium 2,2-dimethylpropyl-1-methacrylate chloride or 2-trimethylammonium methyl methacrylate chloride.

4. The aqueous dispersion according to claim 1, wherein said carboxymethylcellulose has a weight average molecular weight ranging from 5,000–100,000.

5. The aqueous dispersion according to claim 1, wherein said at least one substance (B) is a softener, antiblocking agent, pigment, stabilizer, antioxidant, wetting agent, expanding agent, brightener, aromatic substance or flavoring agent.

6. A method of preparing a shaped drug preparation, comprising:
   coating the surface of a shaped drug material with the aqueous dispersion of claim 1, thereby providing a drug with a quickly disintegrating coating.

7. The method of claim 6, wherein the disintegration time of the drug coating is less than 30 min for an applied polymer coating of 2 mg/$cm^2$ in artificial gastric juice.

8. The method of claim 6, wherein the shaped drug material is in the shape of a capsule, a tablet, a granulate, a pellet or a regularly or irregularly shaped crystal.

9. The method of claim 8, wherein the shaped drug material is in the shape of a granulate, pellet or regularly or irregularly shaped crystal of a size ranging from 0.01–2.5 mm.

10. The method of claim 8, wherein the shaped drug material is in the shape of a tablet of a size ranging from 2.5–30.0 mm.

11. The method of claim 8, wherein the dispersion is applied by spraying.

12. A method of preparing a drug formulation, comprising:
  employing the dispersion of claim 1 as a binder for an active pharmaceutical ingredient.

13. A method of preparing a shaped drug preparation, comprising:
  spraying the surface of a shaped core with a the dispersion of claim 1 which contains no active ingredient while simultaneously adding active powdered active ingredient or their mixtures to the core.

14. A shaped pharmaceutical product, comprising:
  a chewable tablet prepared by the method of claim 12.

15. A shaped pharmaceutical product, comprising:
  a sheet drug containing product prepared by the method of claim 12.

16. A method of preparing a redispersible powder, comprising:
  spraying drying the dispersion of claim 1.

17. A redispersible powder prepared by spray drying the dispersion of claim 1.

* * * * *